United States Patent [19]
Evans

[11] Patent Number: 5,223,509
[45] Date of Patent: Jun. 29, 1993

[54] β-CARBOLINES AS CHOLECYSTOKININ AND GASTRIN ANTAGONISTS

[75] Inventor: Ben E. Evans, Lansdale, Pa.

[73] Assignee: Merck & Co., Inc., Rahway, N.J.

[21] Appl. No.: 841,231

[22] Filed: Feb. 21, 1992

Related U.S. Application Data

[63] Continuation of Ser. No. 593,547, Oct. 2, 1990, abandoned, which is a continuation of Ser. No. 363,357, Jun. 2, 1989, abandoned, which is a continuation of Ser. No. 244,583, Sep. 13, 1988, abandoned, which is a continuation of Ser. No. 86,134, Aug. 17, 1987, abandoned.

[51] Int. Cl.$^5$ .................. A61K 31/435; C07D 471/04
[52] U.S. Cl. .................................. 514/292; 514/210; 514/211; 514/255; 514/542; 514/599; 546/85; 546/86; 546/87

[58] Field of Search ............... 514/210, 211, 255, 292, 514/542, 599; 546/85, 86, 87

[56] References Cited

FOREIGN PATENT DOCUMENTS 3240514  5/1984  Fed. Rep. of Germany ........ 546/85

Primary Examiner—Johann Richter
Attorney, Agent, or Firm—Mark R. Daniel; Joseph F. DiPrima

[57] ABSTRACT

This invention relates to certain β-carbolines, which are antagonists of the functions of cholecystokinin (CCK) and gastrin, to pharmaceutical compositions comprising these compounds, and to the use of these compounds in the prevention and treatment of disorders of the gastrointestinal, central nervous and appetite-regulatory systems of mammals, especially of humans.

6 Claims, No Drawings

β-CARBOLINES AS CHOLECYSTOKININ AND GASTRIN ANTAGONISTS

This is a continuation of application Ser. No. 07/593,547, filed Oct. 2, 1990 now abandoned which is a continuation of application Ser. No. 363,357, filed Jun. 2, 1989, now abandoned which is a continuation of application Ser. No. 244,583, filed Sep. 13, 1988, now abandoned which is a continuation of application Ser. No. 086,134, filed Aug. 17, 1987, now abandoned.

BACKGROUND OF THE INVENTION

Cholecystokinins (CCK) and gastrin are structurally-related neuropeptides which exist in gastrointestinal tissue and in the central nervous system (see, V. Mutt, *Gastrointestinal Hormones*, G. B. J. Glass, Ed., Raven Press, N.Y., p. 169 and G. Nisson, ibid, p. 127).

Cholecystokinins include CCK-33, a neuropeptide of thirty-three amino acids in its originally isolated form (see, Mutt and Jorpes, *Biochem. J.* 125, 678 (1971)), its carboxylterminal octapeptide, CCK-8 (a naturally-occuring neuropeptide, also, and the minimum fully active sequence), and 39- and 12-amino acid forms, while gastrin occurs in 34-, 17- and 14-amino acid forms, with the minimum active sequence being the C-terminal pentapeptide, Gly-Trp-Met-Asp-Phe-NH$_2$, which is the common structural element shared by both CCK and gastrin.

CCK's are believed to be physiological satiety hormones, thereby possibly playing an important role in appetite regulation (G. P. Smith, *Eating and Its Disorders*, A. J. Stunkard and E. Stellar, Eds, Raven Press, New York, 1984, p. 67), as well as also stimulating colonic motility, gall bladder contraction, pancreatic enzyme secretion, and inhibiting gastric emptying. They reportedly co-exist with dopamine in certain mid-brain neurons and thus may also play a role in the functioning of dopaminergic systems in the brain, in addition to serving as neurotransmitters in their own right (see: A. J. Prange et al., "Peptides in the Central Nervous System", *Ann. Repts. Med. Chem.* 17, 31, 33 [1982] and references cited therein; J. A. Williams, *Biomed. Res.* 3 107 [1982]); and J. E. Morley, *Life Sci.* 30, 479, [1982]).

The primary role of gastrin, on the other hand, appears to be stimulation of the secretion of water and electrolytes from the stomach, and, as such, it is involved in control of gastric acid and pepsin secretion. Other physiological effects of gastrin then include increased mucosal blood flow and increased antral motility, with rat studies having shown that gastrin has a positive trophic effect on the gastric mucosa, as evidenced by increased DNA, RNA and protein synthesis.

Antagonists to CCK and to gastrin have been useful for preventing and treating CCK-related and/or gastrin-related disorders of the gastrointestinal (GI) and central nervous (CNS) systems of animals, especially of humans. Just as there is some overlap in the biological activities of CCK and gastrin, antagonists also tend to have affinity for both receptors. In a practical sense, however, compounds of the present invention exhibit sufficient selectivity for specific CCK or gastrin receptors.

Selective CCK antagonists are themselves useful in treating CCK-related disorders of the appetite regulatory systems of animals as well as in potentiating and prolonging opiate-mediated analgesia, reversing tolerance to opiates, and inducing analgesia themselves, thus having utility in the treatment of pain [see P. L. Faris et al., *Science* 226, 1215 (1984)], while selective gastrin antagonists are useful in the modulation of CNS behavior, as a palliative for gastrointestinal neoplasms, and in the treatment and prevention of gastrin-related disorders of the gastrointestinal system in humans and animals, such as peptic ulcers, Zollinger-Ellison syndrome, antral G cell hyperplasia and other conditions in which reduced gastrin activity is of therapeutic value.

Also, since CCK and gastrin also have trophic effects on certain tumors [K. Okyama, *Hokkaido J. Med. Sci.*, 60, 206–216 (1985)], antagonists of CCK and gastrin are useful in treating these tumors [see, R. D. Beauchamp et al., *Ann. Surg.*, 202,203 (1985)].

Four distinct chemical classes of CCK-receptor antagonists have been reported. The first class comprises derivatives of cyclic nucleotides, of which dibutyryl cyclic GMP has been shown to be the most potent by detailed structur-function studies (see, N. Barlos et al., *Am. J. Physiol.*, 242, G 161 (1982) and P. Robberecht et al., *Mol., Pharmacol.*, 17, 268 (1980)).

The second class comprises peptide antagonists which are C-terminal fragments and analogs of CCK, of which both shorter (Boc-Met-Asp-Phe-NH$_2$, Met-Asp-Phe-NH$_2$), and longer (Cbz-Tyr(SO$_3$H)-Met-Gly-Trp-Met-Asp-NH$_2$) C-terminal fragments of CCK can function as CCK antagonists, according to recent structure-function studies (see, R. T. Jensen et al., *Biochem. Biophys. Acta.*, 757, 250 (1983), and M. Spanarkel et al., *J. Biol. Chem.*, 258, 6746 (1983)). The latter compound was recently reported to be a partial agonist [see, J. M. Howard et al., *Gastroenterology* 86(5) Part 2, 1118 (1984)].

Then, the third class of CCK-receptor antagonists comprises the amino acid derivatives: proglumide, a derivative of glutaramic acid, and the N-acyl tryptophans including para-chlorobenzoyl L-tryptophan (benzotript), [see, W. F. Hahne et al., Proc. Natl. Acad. Sci. U.S.A.., 87, 6304 (1981), R. T. Jensen et al., *Biochem. Biophys. Acta.*, 761, 269 (1983)]. All of these compounds, however, are relatively weak antagonists of CCK IC$_{50}$: generally 10$^{-4}$M[although more potent analogs of proglumide have been recently reported in F. Makovec et al., *Arzneim-Forsch Drug Res.*, 35 (II), 1048 (1985) and in German Patent Application DE 3522506A1], but down to 10$^{-6}$M in the case of peptides), and the peptide CCK-antagonists have substantial stability and absorption problems.

In addition, a fourth class consists of improved CCK-antagonists comprising a nonpeptide of novel structure from fermentation sources [R. S. L. Chang et al., *Science*, 230, 177–179 (1985)] and 3-substituted benzodiazepines based on this structure [published European Patent Applications 167 919, 167 920 and 169 392, B. E. Evans et al, *Proc. Natl. Acad. Sci. U.S.A.*, 83, p. 4918–4922 (1986) and R. S. L. Chang et al, ibid, p. 4923–4926] have also been reported.

No really effective receptor antagonists of the in vivo effects of gastrin have been reported (J. S. Morley, *Gut Pept. Ulcer Proc.*, Hiroshima Symp. 2and 1983, p. 1), and very weak in vitro antagonists, such as proglumide and certain peptides have been described [(J. Martinez, *J. Med. Chem.* 27, 1597 (1984)]. Recently, however, pseudopeptide analogs of tetragastrin have been reported to be more effective gastrin antagonists than previous agents [J. Martinez et al., *J. Med. Chem.*, 28, 1874–1879 (1985)].

A small number of peptide CCK/gastrin antagonists have been reported, all of which are truncated CCK-8 sequences. The most potent of these peptides is Cbz-Tyr(SO₃H)-Met-Gly-Trp-Met-Asp-NH₂. However, this sequence and others of this type are liable to degradation by proteases, thus limiting the duration of activity of these peptides.

It was, therefore, an object of this invention to identify substances which more effectively antagonize the function of cholecystokinins in disease states in mammals, especially in humans. It was another object of this invention to prepare novel compounds which inhibit cholecystokinins and antagonize the function of gastrin. It was still another object of this invention to develop a method of antagonizing the functions of cholecystokinin/gastrin in disease states in mammals. It is also an object of this invention to develop a method of preventing or treating disorders of the gastrointestinal, central nervous and appetite regulatory systems of mammals, especially of humans.

SUMMARY OF THE INVENTION

The instant invention is directed to certain β-carbolines, which are antagonists of the functions of cholecystokinin (CCK) and gastrin, to pharmaceutical compositions comprising these compounds, and to the use of these compounds in the prevention and treatment of disorders of the gastrointestinal, central nervous and appetite-regulatory systems of mammals, especially of humans, including, for instance, irritable bowel syndrome, excess pancreatic or gastric secretions, acute pancreatitis, gastrointestinal ulcers, motility disorders, neuroleptic disorders, tardive dyskinesia, Parkinson's disease, psychosis, Gilles de la Tourette Syndrome, pain, Zollinger Ellison syndrome, gastroesophageal reflux disease and antral G cell hyperplasia, and malignancies of the lower esophagus, stomach, intestines and colon and potentiating and prolonging opiate mediated analgesia and reversing tolerance to opiates.

DETAILED DESCRIPTION OF THE INVENTION

The present invention relates to a method of antagonizing the binding of cholecystokinins to cholecystokinin receptors or antagonizing the binding of gastrin to gastrin receptors which comprises contacting said cholecystokinin receptors or said gastrin receptors, respectively, with a compound represented by formula I:

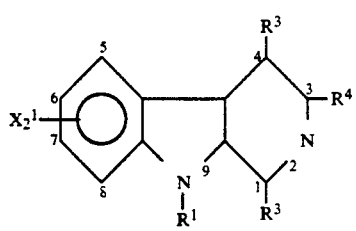
(I)

wherein:
each $X^1$ is independently selected from the group consisting of H, Cl, Br, F, I, NO₂, CF₃, NH₂, CH₃, C₁₋₄ straight or branched chain alkoxy, alkyl or alkylthio, and CN;
$R^1$ is H, C₁₋₄ straight or branched chain alkyl,

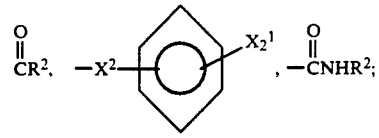

each $R^2$ is independently selected from the group consisting of C₁₋₄ linear or branched chain alkyl, phenyl,

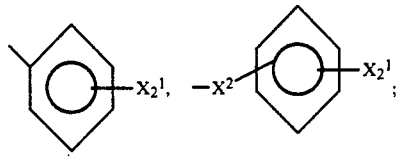

each $X^2$ is independently selected from the group consisting of C₁₋₄ linear or branched alkylidene;
each $R^3$ is independently selected from the group consisting of: H, C₁₋₄ linear or branched alkyl,

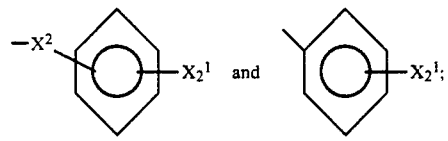

$R^4$ is selected from the group consisting of:

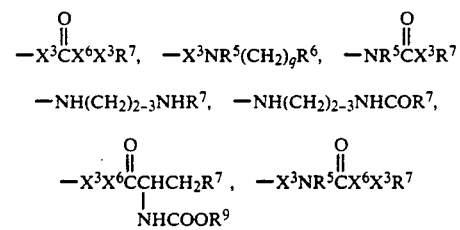

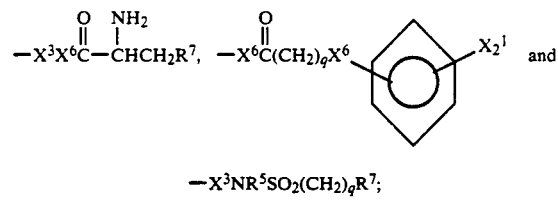

$R^5$ is H or C₁₋₄ linear or branched chain alkyl;
$R^6$ is alpha or beta naphthyl or 2-indolyl;
q is 0–4;
$R^7$ is α- or β-naphthyl, substituted or unsubstituted phenyl (wherein the substituents may be 1 to 2 of halo, —NO₂, —OH, —X³NR¹⁰R¹¹, C₁₋₄ linear or branched chain alkyl, CF₃, CN, SCF₃, C≡CH, CH₂SCF₃,

OCCH₃,

OCHF₂, SH, SPh, PO₃H, C₁₋₄ linear or branched chain alkoxy, C₁₋₄ linear or branched chain alkylthio or COOH), 2-, 3-, 4-pyridyl,

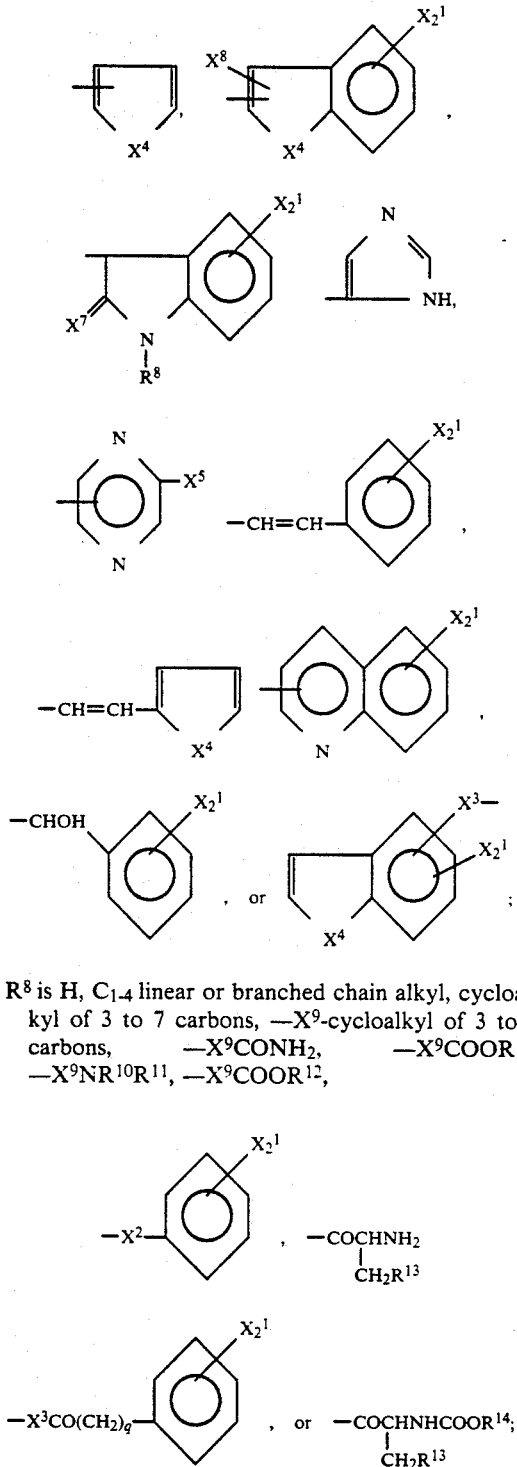

R[8] is H, $C_{1-4}$ linear or branched chain alkyl, cycloalkyl of 3 to 7 carbons, —X[9]-cycloalkyl of 3 to 7 carbons, —X[9]CONH$_2$, —X[9]COOR[12], —X[9]NR[10]R[11], —X[9]COOR[12],

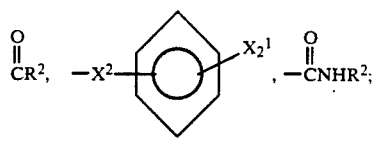, —COCHNH$_2$ | CH$_2$R[13]

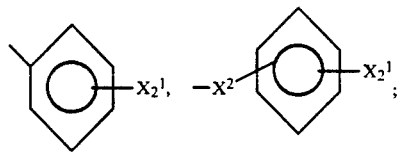, or —COCHNHCOOR[14]; | CH$_2$R[13]

R[9] is $C_{1-4}$ linear or branched chain alkyl or phenyl $C_{1-4}$ linear or branched chain alkyl;

R[10] and R[11] are independently R[12] or in combination with the N of the NR[10]R[11] group form an unsubstituted or mono or disubstituted, saturated or unsaturated, 4-7 membered heterocyclic ring, or benzofused 4-7 membered heterocyclic ring or said heterocyclic ring or said benzofused heterocyclic ring which further comprises a second heteroatom selected from O and NCH$_3$ and the substituent(s) is/are independently selected from $C_{1-4}$ alkyl;

R[12] is H, $C_{1-4}$ linear or branched chain alkyl, cycloalkyl of 3 to 7 carbons, substituted or unsubstituted phenyl, or substituted or unsubstituted phenyl $C_{1-4}$ linear or branched chain alkyl wherein the phenyl or phenyl $C_{1-4}$ linear or branched chain alkyl substituents may be 1 or 2 of halo, $C_{1-4}$ linear or branched chain alkyl, $C_{1-4}$ linear or branched chain alkoxy, nitro, or CF$_3$;

R[13] and R[14] are independently $C_{1-4}$ linear or branched chain alkyl or cycloalkyl of 3 to 7 carbons;

X[3] is absent or $C_{1-4}$ linear or branched alkylidene;

X[4] is S, O, CH$_2$ or NR[8];

X[5] is H, CF$_3$, CN, —COOR[12], NO$_2$ or halo; each X[6] is independently NR[5] or O;

X[7] is O or HH;

X[8] is H or $C_{1-4}$ linear or branched chain alkyl; and

X[9] is $C_{1-4}$ linear or branched chain alkylidene.

Also within the scope of the subject invention are the novel β-carbolines of formula I:

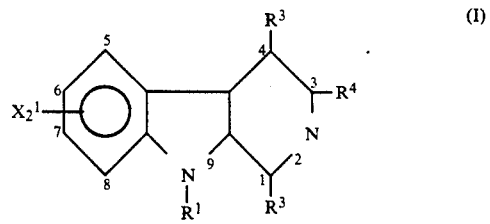

wherein:
each X[1] is independently selected from the group consisting of H, Cl, Br, F, I, NO$_2$, CF$_3$, NH$_2$, CH$_3$, $C_{1-4}$ straight or branched chain alkoxy, alkyl or alkylthio, and CN;

R[1] is H, $C_{1-4}$ straight or branched chain alkyl, $\overset{O}{\underset{}{\overset{\|}{C}}}R^2$, —X[2]—⬡—X$_2^1$, —$\overset{O}{\underset{}{\overset{\|}{C}}}NHR^2$;

each R[2] is independently selected from the group consisting of $C_{1-4}$ linear or branched chain alkyl, phenyl,

⬡—X$_2^1$, —X[2]—⬡—X$_2^1$;

each X[2] is independently selected from the group consisting of $C_{1-4}$ linear or branched alkylidene;

each R[3] is independently selected from the group consisting of: H, $C_{1-4}$ linear or branched alkyl,

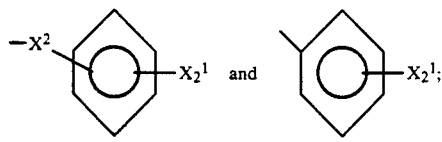 and $R^4$ is selected from the group consisting of:

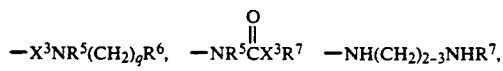

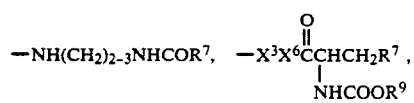

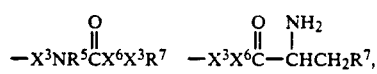

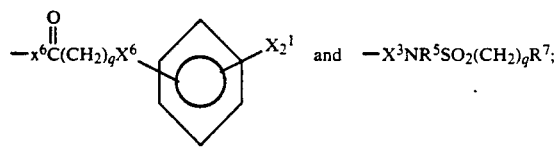 and $-X^3NR^5SO_2(CH_2)_qR^7$;

$R^5$ is H or $C_{1-4}$ linear or branched chain alkyl;
$R^6$ is alpha or beta naphthyl or 2-indolyl;
q is 0–4;
$R^7$ is α- or β-naphthyl, substituted or unsubstituted phenyl (wherein the substituents may be 1 or 2 of halo, $-NO_2$, $-OH$, $-X^3NR^{10}R^{11}$, $C_{1-4}$ linear or branched chain alkyl, $CF_3$, CN, $SCF_3$, C≡CH, $CH_2SCF_3$,

$OCHF_2$, SH, SPh, $PO_3H$, $C_{1-4}$ linear or branched chain alkoxy, $C_{1-4}$ linear or branched chain alkylthio or COOH), 2-, 3-, 4-pyridyl,

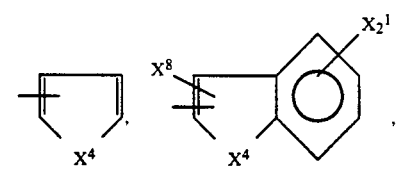

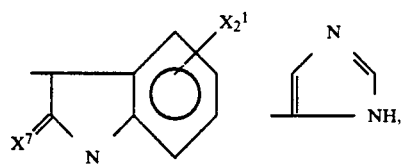

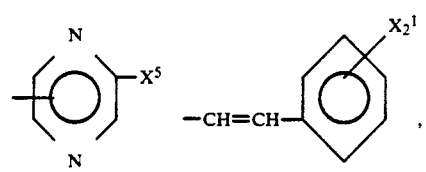

-continued

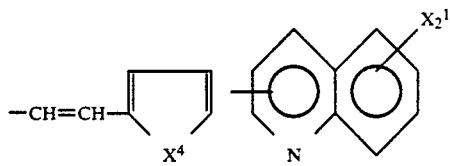

$R^8$ is H, $C_{1-4}$ linear or branched chain alkyl, cycloalkyl of 3 to 7 carbons, $-X^9$-cycloalkyl or 3 to 7 carbons, $-X^9CONH_2$, $-X^9COOR^{12}$, $-X^9NR^{10}R^{11}$, $-X^9COOR^{12}$,

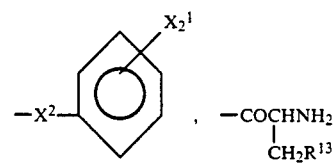

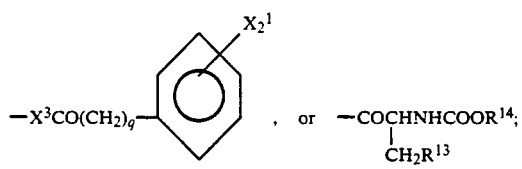

$R^9$ is $C_{1-4}$ linear or branched chain alkyl or phenyl $C_{1-4}$ linear or branched chain alkyl;
$R^{10}$ and $R^{11}$ are independently $R^{12}$ or in combination with the N or the $NR^{10}R^{11}$ group form an unsubstituted or mono or disubstituted, saturated or unsaturated, 4–7 membered heterocyclic ring, or benzofused 4–7 membered heterocyclic ring or said heterocyclic ring or said benzofused heterocyclic ring which further comprises a second heteroatom selected from O and $NCH_3$ and the substituent(s) is/are independently selected from $C_{1-4}$ alkyl;
$R^{12}$ is H, $C_{1-4}$ linear or branched chain alkyl, cycloalkyl of 3 to 7 carbons, substituted or unsubstituted phenyl, or substituted or unsubstituted phenyl $C_{1-4}$ linear or branched chain alkyl wherein the phenyl or phenyl $C_{1-4}$ linear or branched chain alkyl substituents may be 1 or 2 of halo, $C_{1-4}$ linear or branched chain alkyl, $C_{1-4}$ linear or branched chain alkoxy, nitro, or $CF_3$;
$R^{13}$ and $R^{14}$ are independently $C_{1-4}$ linear or branched chain alkyl or cycloalkyl of 3 to 7 carbons;
$X^3$ is absent or $C_{1-4}$ linear or branched alkylidene;
$X^4$ is S, O, $CH_2$ or $NR^8$;
$X^5$ is H, $CF_3$, CN, $-COOR^{12}$, $NO_2$ or halo; each $X^6$ is independently $NR^5$ or O;
$X^7$ is O or HH;
$X^8$ is H or $C_{1-4}$ linear or branched chain alkyl;
$X^9$ is $C_{1-4}$ linear or branched chain alkylidene; with the proviso that when $X^1$ is H, $R^1$ is H, each $R^3$ is H, then $R^4$ is not

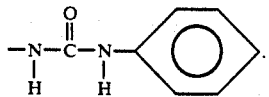

Preferred compounds of Formula I include those wherein $X^1$ is H, $R^1$ is H, $R^3$ is H and $R^4$ is

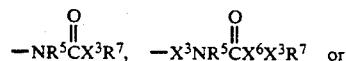

or

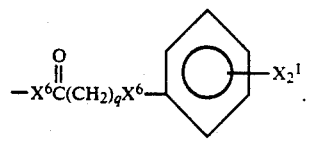

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The ability of the compounds of Formula I to antagonize CCK and gastrin makes these compounds useful as pharmaceutical agents for mammals, especially for humans, for the treatment and prevention of disorders wherein CCK and/or gastrin may be involved. Examples of such disease states include gastrointestinal disorders, especially such as irritable bowel syndrome, gastroesophageal reflux disease or ulcers, excess pancreatic or gastric secretion, acute pancreatitis, or motility disorders; central nervous system disorders, caused by CCK interactions with dopamine, such as neuroleptic disorders, tardive dyskinesia, Parkinson's disease, psychosis or Gilles de la Tourette Syndrome; disorders of appetite regulatory systems; Zollinger-Ellison syndrome, antral G cell hyperplasia, or pain (potentiation of opiate analgesia); as well as certain tumors of the lower esophagus, stomach, intestines and colon.

The compounds of Formula I thereof, may be administered to a human subject either alone or, preferably, in combination with pharmaceutically-acceptable carriers or diluents, optionally with known adjuvants, such as alum, in a pharmaceutical composition, according to standard pharmaceutical practice. The compounds can be administered orally or parenterally, including intravenous, intramuscular, intraperitoneal, subcutaneous and topical administration.

For oral use of an antagonist of CCK, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

When a compound according to Formula I is used as an antagonist of CCK or gastrin in a human subject, the daily dosage will normally be determined by the prescribing physician with the dosage generally varying according to the age, weight, and response of the individual patient, as well as the severity of the patient's symptoms. However, in most instances, an effective daily dosage will be in the range of from about 0.05 mg/kg to about 50 mg/kg of body weight, and preferably, of from 0.5 mg/kg to about 20 mg/kg of body weight, administered in single or divided doses. In some cases, however, it may be necessary to use dosages outside these limits.

In the treatment of irritable bowel syndrome, for instance, 0.1 to 10 mg/kg of a CCK antagonist might be administered orally (p.o.), divided into two doses per day (b.i.d.). In treating delayed gastric emptying, the dosage range would probably be the same, although the drug might be administered either intravenously (I.V.) or orally, with the I.V. dose probably tending to be slightly lower due to better availability. Acute pancreatitis might be treated preferentially by an I.V. form, whereas spasm and/or reflex esophageal, chronic pancreatitis, post vagotomy diarrhea, anorexia or pain associated with biliary dyskinesia might indicate p.o. form administration.

In the use of a gastrin antagonist as a tumor palliative for gastrointestinal neoplasms with gastrin receptors, as a modulator of central nervous system activity, treatment of Zollinger-Ellison syndrome, or in the treatment of peptic ulcer disease, a dosage of 0.1 to 10 mg/kg administered one-to-four times daily might be indicated.

Because these compounds antagonize the function of CCK in animals, they may also be used as feed additives to increase the food intake of animals in daily dosage of approximately 0.05 to 50 mg/kg of body weight.

The compounds of Formula I are prepared according to the following schemes.

SCHEME I
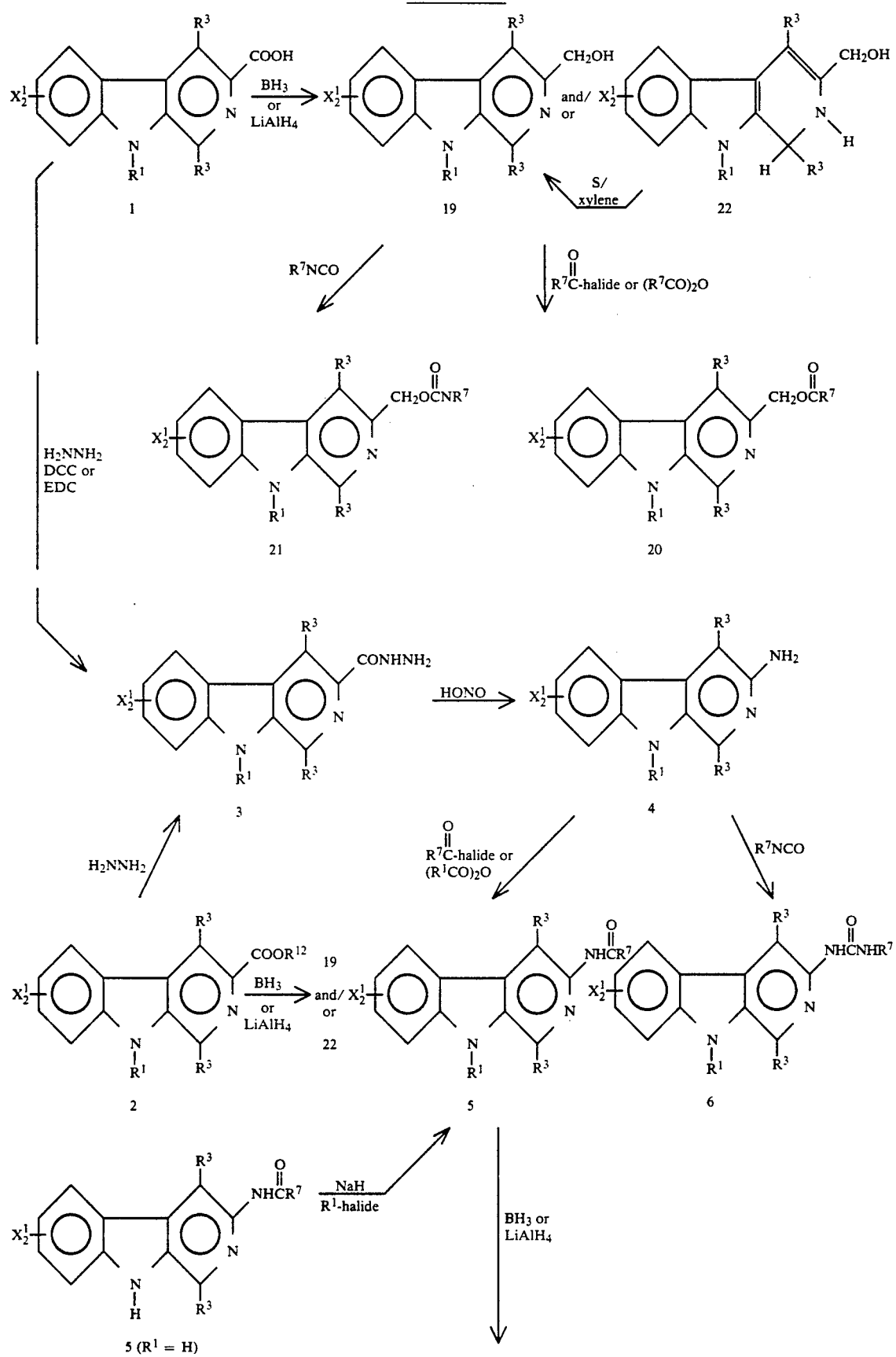

-continued
SCHEME I
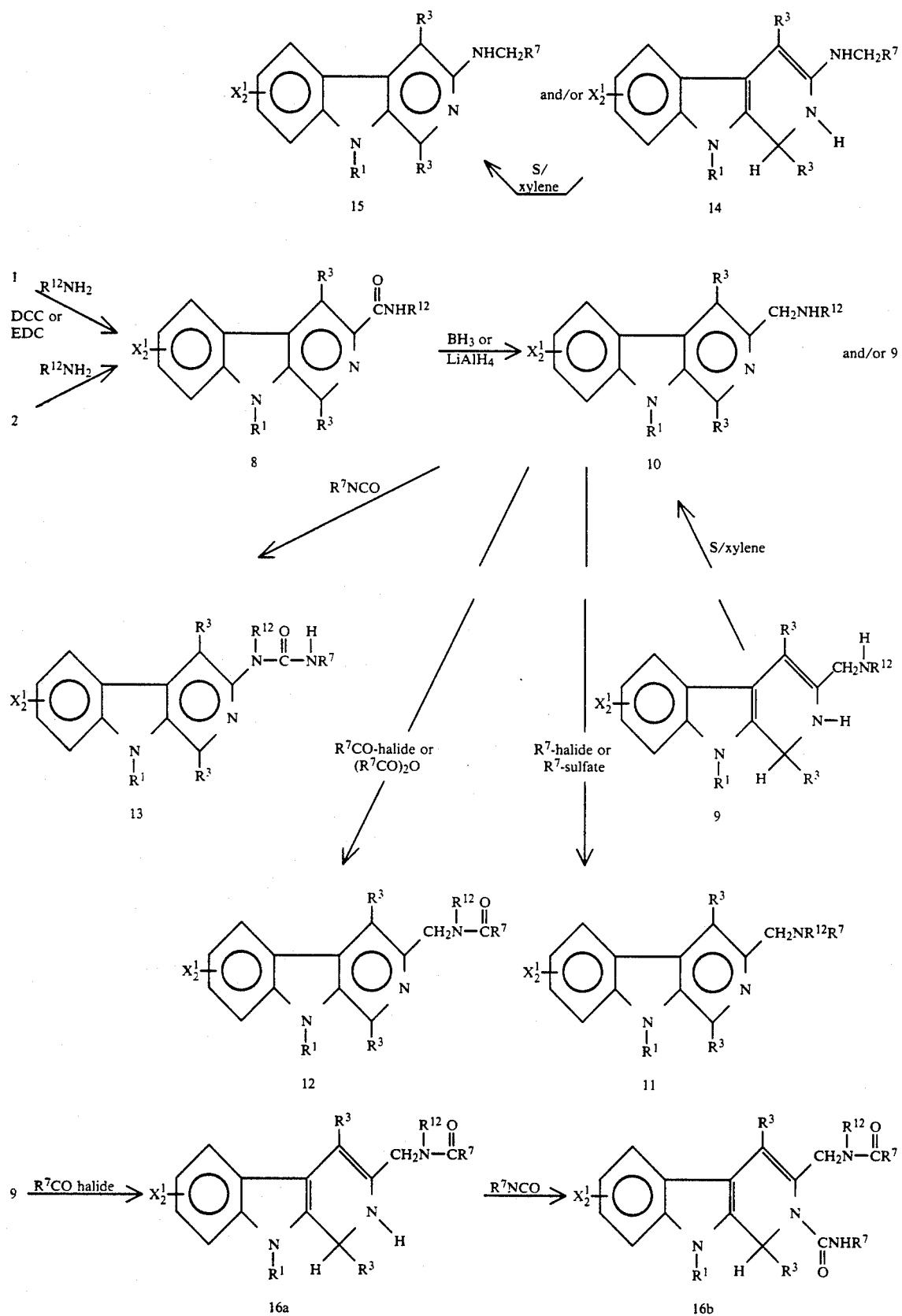

-continued
SCHEME 1

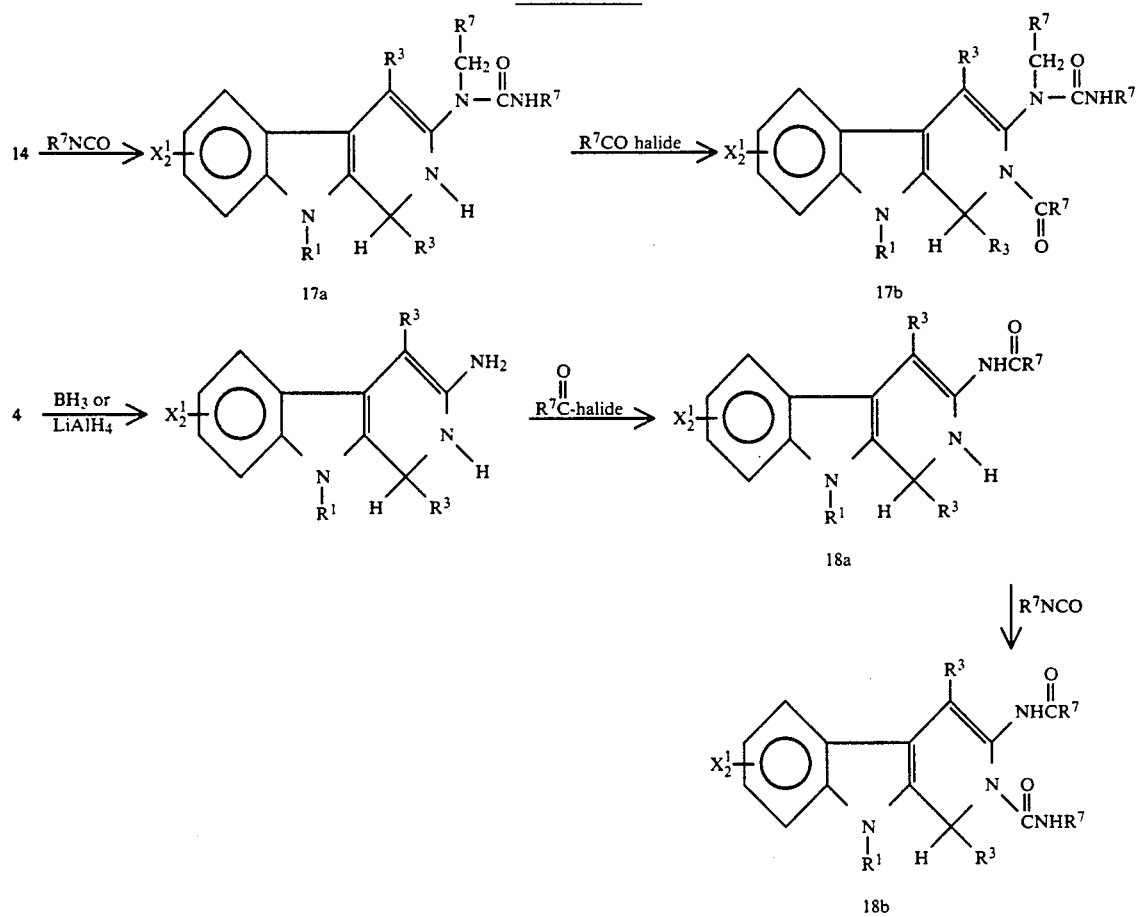

The synthesis and chemical transformations of β-carbolines are reviewed in "Advances in Heterocyclic Chemistry", Vol. 3, A. R. Katritzky, ed., N. Y., Academic Press, 1964, pp. 79-207 and in "Heterocyclic Compounds", Vol. 7, R. C. Elderfield, ed., N. Y., John Wiley and Sons, 1961, pp. 247-282. β-Carboline-3-carboxylic acids and the esters from which they are readily derived by hydrolysis are well known in the art. 9-Alkyl and acyl derivatives, for example, are described in Biere et. al., Liebig's Ann. Chem., 1749-64, 1986, Dupas et. al., J. Heterocyclic Chem., 20, 967-970, 1983, Stack et. al., Abstr. Pap. Am. Chem. Soc. (192 Meet., MEDI 74, 1986), and Eder et. al., Eur. Appl. 0030254. Examples containing alkyl or aryl substituents at $C_1$ are described in Borea and Ferretti, Biochem. Pharmacol., 35, 2836-2839, 1986. Examples containing $C_4$ substituents such as alkyl, alkoxy, alkoxymethyl, etc. are described in Huth et. al., U.S. Pat. No. 4,600,715, Huth et. al., U.S. Pat. No. 4,623,649, Biere, DE 3240511A1, Braestrup et. al., U.S. Pat. No. 4,435,403, and Eder et. al., Eur. Appl. 0030254. Examples containing substituents in the benzene ring at $C_5$, $C_6$, $C_7$, or $C_8$ which include halo, nitro, cyano, alkyl, cycloalkyl, trifluoromethyl, methylthio, amino, mono- and dialkylamino, alkoxy, benzyloxy, etc. are described in Huth et. al., U.S. Pat. No. 4,600,715, Huth et. al., U.S. Pat. No. 4,623,649, Biere, DE 3240511A1, Braestrup et. al., U.S. Pat. No. 4,435,403, Eder et. al., Eur. Appl. 0030254, Szuszkovicz and Youngdale, U.S. Pat. No. 3,202,667, Shannon et. al., Abstr. Pap. Am. Chem. Soc. (191 Meet., MEDI 51, 1986), Hagen et. al., Abstr. Pap. Am. Chem. Soc. (190 Meet., MEDI 86, 1985), and Dodd et. al., J. Med. Chem., 28, 824-828, 1985. These compounds are the starting materials 1 and 2 for preparation of the compounds of the present invention according to Scheme 1.

As shown in Scheme 1, substituted or unsubstituted β-carboline-3-carboxylic acids 1 are converted to the hydrazides 3 by treatment with hydrazine and a suitable coupling agent such as dicyclohexylcarbodiimide (DCC) or 1-ethyl-3-(3-dimethylaminopropyl)-carbodiimide hydrochloride (EDC) in the presence or absence of auxiliary agents such as N-hydroxybenzotriazole (HBT). Triethyl amine or another amine is added to adjust the pH to 4-10. Suitable solvents include DMF and $CH_2Cl_2$.

Alternatively, β-carboline-3-carboxylic esters 2, substituted or unsubstituted at other sites in the molecule, are converted to the hydrazides 3 by treatment with hydrazine in a suitable solvent such as DMF or methanol.

Hydrazides 3 are converted to amines 4 by treatment with sodium nitrite in acid or by other suitable nitrosating agent, followed by heating in aqueous acetic acid or other suitable medium, according to the procedure of Dodd et. al., (J. Med. Chem., 28, 824-828, 1985). The resulting amines 4 are acylated by treatment with acid halides or anhydrides to give the amides 5. Alternatively, amines 4 are acylated with isocyanates to give ureas 6.

Where $R^1$ is H, additional $R^1$ substituents may be appended to amides 5 and ureas 6 by treatment with a suitable base, such as sodium hydride, followed by an alkyl or acyl halide or acyl anhydride, all in a suitable solvent such as DMF.

Amides 8 can be prepared by treatment of esters 2 with ammonia or a primary or secondary amine, or by treatment of acids 1 with such amines in the presence of a suitable coupling reagent such as DCC or EDC. This coupling also can be carried out using carbonyldiimidazole as described by Lippke et al., J. Pharm. Sci., 74, 676, 1985 and Arch. Pharm., 320, No. 2, 145, 1987. Homologs of amides 8 in which the amide carbonyl group is linked to the β-carboline ring by a chain of one or more alkylidene groups are obtained from the corresponding homologs of acids 1. These in turn are obtained from the acids 1 by homologation using techniques well known in the art, as for example the homologation using diazomethane, known as the Arndt-Eistert reaction, which is reviewed by Bachmann and Struve in "Organic Reactions", Vol. 1, R. Adams et al., eds., New York, John Wiley and Sons, Inc., 1942, pp. 38-62.

The amides 8 can be reduced with borane in tetrahydrofuran or with lithium aluminum hydride to give the amines 10. In cases where reduction of the 6-membered heterocyclic ring also occurs, the resulting reduced-ring compounds 9 may be reoxidized to the aromatic form 10 by treatment with a suitable oxidizing agent such as sulfur in xylene or chloranil as described by Snyder et. al., J. Am. Chem. Soc., 70, 219, 1948. The amines 10 can be alkylated with alkyl halides or sulfates to give the alkyl derivatives 11. Alternatively, the amines 10 can be acylated with acyl halides or anhydrides to give the amides 12, or with isocyanates to give ureas 13.

Amides 5 can be similarly reduced to the amines 15, using reoxidation of the ring-reduced compounds 14 where necessary as described above for 9. The reduced-ring amines 9 and 14 can themselves be alkylated or acylated either on the exocyclic amino group or on the nitrogen of the reduced six-membered heterocyclic ring, or both, to give the various alkyl and acyl derivatives, exemplified by 16a-b and 17a-b. Similar reduction and alkylation/acylation of amines 4 gives compounds such as 18a-b.

Esters 2 and/or acids 1 can be similarly reduced to the hydroxymethyl compounds, 19. In the event of overreduction, reoxidation of an intermediate such as 22 can be carried out as described hereinabove. These may be acylated to give esters 20 or carbamates 21.

In Vitro Activity of Compounds of Formula I

The biological activity of the compounds of Formula I have been evaluated using 1.) an $^{125}$I-CCK receptor binding assay and in vitro isolated tissue preparations and 2.) $^{125}$I gastrin and $^3$H-pentagastrin binding assays.

MATERIALS and methods

1. CCK Receptor BindinG (Pancreas)

CCK-33 was radiolabeled with $^{125}$I-Bolton Hunter reagent (2000 Ci/mmole) as described by Sankara et al. (*J. Biol. Chem.* 254: 9349-9351, 1979). Receptor bindinG was performed according to Innis and Snyder (*Proc. Natl. Acad. Sci.* 77: 6917-6921, 1980) with the minor modification of adding the additional protease inhibitors, phenylmethane sulfonyl fluoride and o-phenanthroline. The latter two compounds have no effect on the $^{125}$I-CCK receptor bindinG assay.

Male Sprague-Dawley rats (200-350 g) were sacrificed by decapitation. The whole pancreas was dissected free of fat tissue and was homogenized in 20 volumes of ice-cold 50 mM, Tris HCl (pH 7.7 at 25° C.) with a Brinkmann Polytron PT 10. The homogenates were centrifuged at 48,000 g for 10 min. Pellets were resuspended in Tris Buffer, centrifuged as above and resuspended in 200 volumes of binding assay buffer (50 mM Tris HCl, pH 7.7 at 25° C., 5 mM dithiothrietol, 0.1 mM bacitracin, 1.2 mM phenylmethane sulfonyl fluoride and 0.5 mM o-phenanthroline). For the binding assay, 25 µl of buffer (for total binding) or unlabeled CCK-8 sulfate to give a final concentration of 1 µM (for nonspecific binding) or the compounds of Formula I (for determination of inhibition of $^{125}$I CCK binding) and 25 µl of $^{125}$I-CCK 33 (30,000-40,000 cpm) were added to 450 µl of the membrane suspensions in microfuge tubes. All assays were run in duplicate or triplicate. The reaction mixtures were incubated at 37° C. for 30 minutes and centrifuged in a Beckman Microfuge (4 minutes) immediately after adding 1 ml of ice-cold incubation buffer. The supernatant was aspirated and discarded, pellets were counted with a Beckman gamma 5000. For Scatchard analysis (*Ann. N.Y. Acad. Sci.* 51: 660, 1949), $^{125}$I CCK 33 was progressively diluted with increasing concentrations of CCK 33.

2. CCK Receptor Binding (Brain)

CCK 33 was radiolabeled and the binding was performed according to the description for the pancreas method with modifications according to Saito et al., J. Neurochem. 37:483-490, 1981.

Male Hartley guinea pigs (300-500 g) were sacrificed by decapitation and the brains were removed and placed in ice-cold 50 mM, Tris HCl plus 7.58 g/l Trizma-7.4 (pH 7.4 at 25° C.). Cerebral cortex was dissected and used as a receptor source. Each gram of fresh guinea pig brain tissue was homogenized in 10 ml of Tris/Trizma buffer with a Brinkman polytron PT-10. The homogenates were centrifuged at 42,000 g for 15 minutes. Pellets were resuspended in Tris Buffer, centrifuged as above and resuspended in 200 volumes of binding assay buffer (10 mM N-2-hydroxyethyl-piperazine-N'-2-ethane sulfonic acid (HEPES), 5 mM $MgCl_2$, 0.25 mg/ml bacitracin, 1 mM ethylene glycol-bis-(β-aminoethylether-N,N'-tetraacetic acid) (EGTA), and 0.4% bovine serum albumin (BSA)). For the binding assay, 25 µl of buffer (for total binding) or unlabeled CCK-8 sulfate to give a final concentration of 1 µm (for nonspecific binding) or the compounds of Formula I (for determination of inhibition of $^{125}$I CCK binding) and 25 µl of $^{125}$I-CCK-33 (30,000-40,000 cpm) were added to 450 µl of the membrane suspensions in microfuge tubes. All assays were run in duplicate or triplicate. The reaction mixtures were incubated at 25° C. for 2 hours and centrifuged in a Beckman Microfuge (4 minutes) immediately after adding 1 ml of ice cold incubation buffer. The supernatant was aspirated and discarded, pellets were counted with a Beckman gamma 5000.

The compounds of Formula I can be determined to be competitive antagonists of CCK according to the following assays.

3. Isolated guinea pig gall bladder

Male Hartley guinea pigs (400-600 g) were sacrificed by decapitation. The whole gall bladder was dissected free from adjacent tissues and cut into two equal halves. The gall bladder strips were suspended along the axis of the bile duct in a 5 ml organ bath under 1 g tension. The organ bath contained a Kreb's bicarbonate solution (NaCl 118 mM, KCl 4.75 mM, CaCl 2.54 mM, $KH_2PO_4$ 1.19 mM, Mg $SO_4$ 1.2 mM, $NaHCO_3$ 25 mM and dextrose 11 mM) maintained at 32° C. and bubbled with 95% $O_2$ and 5% $CO_2$. Isometric contractions were recorded using Statham (60 g; 0.12 mm) strain gauges and a Hewlett Packard (77588) recorder. The tissues were washed every 10 minutes for 1 hour to obtain equilibrium prior to the beginning of the study. CCK-8 was added cumulatively to the baths and $EC_{50}$'s determined using regression analysis. After washout (every 10 minutes for 1 hour), the compound of Formula I was added at least 5 minutes before the addition of CCK-8 and the $EC_{50}$ of CCK-8 in the presence of the compound of Formula I similarly determined.

4. Isolated longitudinal muscle of guinea pig ileum

Longitudinal muscle strips with attached nerve plexus were prepared as described in Brit. J. Pharmac. 23:; 356-363, 1964; J. Physiol. 194: 13-33, 1969. Male Hartley guinea pigs were decapitated and the ileum removed (10 cm of the terminal ileum was discarded and the adjacent 20 cm piece used). A piece (10 cm) of the ileum was stretched on a glass pipette. Using a cotton applicator to stroke tangentially away from the mesentery attachment at one end, the longitudinal muscle was separated from the underlying circular muscle. The longitudinal muscle was then tied to a thread and by gently pulling, stripped away from the entire muscle. A piece of approximately 2 cm was suspended in 5 ml organ bath containing Krebs solution and bubbled with 95% $O_2$ and 5% $CO_2$ at 37° C. under 0.5 g tension. CCK-8 was added cumulatively to the baths and $EC_{50}$ values in the presence and absence of compounds of Formula I determined as described in the gall bladder protocol (above).

Gastrin Antagonism

Gastrin antagonist activity of compounds of Formula I was determined using the following assay.

Gastrin Receptor Binding in Guinea Pig Gastric Glands
Preparation of guinea pig gastric mucosal glands Guinea pig gastric mucosal glands were prepared by the procedure of Berglingh and Obrink Acta Physiol. Scand. 96: 150 (1976) with a slight modification according to Praissman et al. C. J. Receptor Res. 3: (1983). Gastric mucosa from guinea pigs ( 300-500 g body weight, male Hartley) were washed thoroughly and minced with fine scissors in standard buffer consisting of the following: 130 mM NaCl, 12 mM $NaHCo_3$, 3 mM $NaH_2PO_4$, 3 mM $Na_2HPO_4$, 3 mM $K_2HPO_4$, 2 mM $MgSO_4$, 1 mM $CaCl_2$, 5 mM glucose and 4 mM L-glutamine, 25 mM HEPES at pH 7.4. The minced tissues were washed and then incubated in a 37° C. shaker bath for 40 minutes with the buffer containing 0.1% collagenase and 0.1% BSA and bubbled with 95% $o_2$ and 5% $CO_2$. The tissues were passed twice through a 5 ml glass syringe to liberate the gastric glands, and then filtered through 200 mesh nylon. The filtered glands were centrifuged at 270 g for 5 minutes and washed twice by resuspension and centrifugation.

Binding studies

The washed guinea pig gastric glands prepared as above were resuspended in 25 ml of standard buffer containing 0.25 mg/ml of bacitracin. For binding studies, to 220 µl of gastric glands in triplicate tubes, 10 µl of buffer (for total binding) or gastrin (1 µM final concentration, for nonspecific binding) or test compound and 10 µl of $^{125}$I-gastrin (NEN, 2200 Ci/mmole, 25 pM final) or $^3$H pentagastrin (NEN 22 Ci/mmole, 1 nM final) were added. The tubes were aerated with 95% $O_2$ and 5% $CO_2$ and capped. The reaction mixtures after incubation at 25° C. for 30 minutes were filtered under reduced pressure on glass G/F B filters (Whatman) and immediately washed further with 4×4 ml of standard buffer containing 0.1% BSA. The radioactivity on the filters was measured using a Beckman gamma 5500 for $^{125}$I-gastrin or liquid scintillation counting for $^3$H-pentagastrin.

IN VITRO RESULTS

1. Effect of The Compounds of Formula I on $^{125}$I-CCK-33 receptor binding

The preferred compounds of Formula I are those which inhibited specific $^{125}$I-CCK-33 binding in a concentration dependent manner.

Scatchard analysis of specific $^{125}$I-CCK-33 receptor binding in the absence and presence of the compounds of Formula I indicated the compound of Formula I competitively inhibited specific $^{125}$I-CCK-33 receptor binding since it increased the $K_D$ (dissociation constant) without affecting the $B_{max}$ (maximum receptor number). A $K_i$ value (dissociation constant of inhibitor) of the compounds of Formula I was estimated.

The data of Table 1 were obtained for compounds of Formula I.

TABLE I

| | CCK Receptor Binding Results | | |
|---|---|---|---|
| | $IC_{50}$ (uM) | | |
| Compound of Example | $^{125}$I-CCK Pancreas | $^{125}$I-CCK Brain | $^{125}$I-Gastrin Gastric Glands |
| 1 | — | >100 | 150 |
| 2 | >100 | >100 | >100 |
| 3 | 3.5 | 72 | >100 |
| 4 | 0.085 | >100 | >100 |
| 5 | 9.8 | ~130 | >100 |
| 6 | 0.71 | >100 | >100 |
| 7 | 0.024 | 67 | >100 |
| 8 | 7.1 | 223 | >100 |
| 9 | 0.04 | 34 | 14 |
| 10 | 0.33 | 68 | 35 |

The invention is further defined by reference to the following preparations and examples, which are intended to be illustrative and not limiting.

EXAMPLE 1

Methyl-9H-pyrido(3,4-b)indole-3-carboxylate($\beta$-carboline-3-carboxylic acid, ethyl ester)

The title compound was prepared according to the procedure of Lippke, et al., J. Med. Chem. 26, 499-503 (1983).

Recrystallized from MeCN: med. brown needles m.p. 260-1° C., PMR: consistent with structural assignment with 10% $CH_3CN$. HPLC: 98.4% pure, M.S.: Molecular Ion observed at 226 m/e.

Anal. Calc'd for $C_{13}H_{10}N_2O_2 \cdot 0.1$ $CH_3CN$. C, 68.83; H, 4.51; N, 12.77. Found: C, 68.87; H, 4.42; N, 12.64.

EXAMPLE 2

3-Amino-9H-pyrido(3,4-b)indole (3-Amino-βcarboline)

The title compound was prepared according to the procedure of Dodd, et al., J. Med. Chem., 29, 824–8 (1985). Yellow solid from EtOH m.p. 292°–4° C. (lit 289°–291° C.) PMR: confirms structural assignment. HPLC: 99.4% pure. M.S: Molecular Ion observed at 183 m/e.

Anal. Calc'd for $C_{11}H_9N_3$: C, 72.11; H, 4.95; N, 22.94 Found: C, 71.84; H, 4.99; N, 22.68

EXAMPLE 3

4-Chloro-N-9H-pyrido(3.4-b)indol-3-yl-benzamide

A solution of 100 mg (0.546 mmol) of 3-amino-N-9H-pyrido(3,4-b)indole in 3 ml $CH_2Cl_2$ and 3 ml of pyridine was treated with 80 ml (0.628 mmol) of p-chlorobenzoylchloride. After stirring 1 hour at 25° C. a second 80 ml portion of p-chlorobenzoylchloride was added and the reaction stirred 1 hour longer.

The solvent was removed in vacuo, the residue treated sat'd $NaHCO_3$ (aq.) and extracted 333 EtOAc. The combined organics were washed $1 \times H_2O$, $1 \times$ Brine, dried over $Na_2SO_4$, filtered and stripped to dryness in vacuo. The crude solid (220 mg) was flash chromatographed on silica gel ($CH_2Cl_2$/EtOAc at 1/1) to give the title compound as light yellow crystals from ether. m.p. 230°–1° C. NMR: consistent with structural assignment. HPLC: 99.8% pure. M.S.: Molecular Ion observed at 321 m/e.

Anal. Calc'd for $C_{18}H_{12}ClN_3O$: C, 67.19; H, 3.76; N, 13.06. Found: c, 67.10; H. 3.76; N, 12.85. TLC: Silica GF (90/10/1/1 of $CH_2Cl_2$/Mech/$H_20$/HOAc), $R_f = 0.54$.

EXAMPLE 4

N-(4-Chlorophenyl)-$N^1$9-H-pyrido(3,4-b)indol-3-yl-urea

A suspension of 75 mg (0.409 mmol) 3-amino-N-9H-pyrido(3,4-b)indole in 4 ml THF was treated with a 1 ml THF solution of 69.1 mg (0.450 mmol) of p-chlorophenylisocyanate. After stirring 15 minutes at 25° C. the solvent was removed in vacuo. The residue was treated with $H_2O$ and extracted 333 EtOAc. The combined extracts were washed $1 \times$ with $H_2O$ and 133 with brine, dried over $Na_2SO_4$, filtered and the filtrate stripped to dryness in vacuo. The crude solid was recrystallized from EtOAc to give the title compound as fine white needles. M.p. >300° C. NMR: Consistent with structural assignment. HPLC: 100% pure. M.S.: Molecular Ion observed at 336 m/e.

Anal. Calc'd for: $C_{18}H_{13}ClN_4O$: C, 64.19; H, 3.89; N, 16.64. Found: C, 64.01; H, 3.99; N, 16.34. TLC: Silica GF (90/10/1/1 of $CH_2Cl_2$/MeOH/HoAc/$H_2O$) Rf=0.58.

EXAMPLE 5

N-9H-Pyrido(3,4-b)indol-3-yl 2 thiophene Carboxamide

3-Amino-N-9H pyrido(3,4-b)indole was treated according to the procedure of Example 3 using thiophene 2-carbonylchloride in place of p-chlorobenzoylchloride. Flash chromatography of the crude product on silica gel ($CH_2Cl_2$/$Et_2O$, 1/1) gave the title compound as an off-white solid. M.p. 109°–125° C. NMR: consistent with structural assignment. HPLC: 99.9% pure. M.S.: Molecular Ion observed at 293 m/e.

Anal. Calc'd for: $C_{16}H_{11}N_3OS$: C, 65.51; H, 3.78; N, 14.33. Found: C, 65.76; H, 3.98; N, 14.29. TLC: Silica GF (90/10/1/1 of $CH_2Cl_2$/MeOH/$H_2O$/HoAc) Rf=0.56.

EXAMPLE 6

N-9H-Pyrido(3,4-b)indol-3-yl-1-methyl-1H-indole-2-carboxamide

3-Amino-N-9H-pyrido(3,4-b)indole was treated according to the procedure of Example 3 using N-methylindole 2-carbonylchloride in place of p-chlorobenzoylchloride. The product was recrystallized from MeOH to give the title compound as a tan solid. M.p. 300°–1° C. NMR: consistent with structural assignment. HPLC: 100% pure. M.S.: Molecular Ion observed at 340 m/e.

Anal Calc'd for: $C_{21}H_{16}N_4O$: C, 74.10; H, 4.74; N, 16.46. Found: C, 73.90; H, 5.00; N, 16.41. TLC: Silica GF (90/10/1/1 of $CH_2Cl_2$/MeOH/$H_2O$/HoAc) Rf=0.62.

EXAMPLE 7

N-9H-Pyrido(3,4-b)indol-3-yl-1H-indole 3-acetamide

3-Amino-N-9H pyrido(3,4-b)indole was treated according to the procedure of Example 3 using indole 3-acetylchloride in place of p-chlorobenzoyl-chloride. Flash chromatography of the crude product on silica gel ($CH_2Cl_2$/EtOAc, 35/65) gave the title compound as a tan solid from EtOAc. M.p. 252–4° C. NMR: Consistent with structural assignment including ethyl acetate solvate. HPLC: 99.6% pure. M.S.: Molecular ion observed at 340 m/e.

Anal Calc'd for: $C_{21}H_{16}N_4O \cdot 0.15\ C_4H_8O_2$: C, 73.37; H, 4.90; N, 15.85. Found: C, 73.37; H, 4.95; N, 16.01. TLC: Silica GF (90/10/1/1 of $CH_2Cl_2$/MeOH/$H_2O$/HoAc) Rf=0.48.

EXAMPLE 8

N-9H-Pyrido(3,4-b)indol-3-yl benzamide

3-Amino-N-9H pyrido(3,4-b)indole was treated according to the procedure of Example 3 using benzoylchloride in place of p-chlorobenzoylchloride. Flash chromatography of the crude product on silica gel ($CH_2Cl_2$/EtOAc 60/40) gave the title compound as light yellow crystals from ether. M.p. 97°–100° C. NMR: consistent with structural assignment including ether soluate. HPLC: 96.3% pure. M.S.: Molecular ion observed at 287 m/e.

Anal Calc'd for: $C_{18}H_{13}N_3O \cdot 0.5\ C_4H_{10}O$: C, 74.05; H, 5.59; N, 12.96. Found: C, 74.24; H, 5.87; N, 12.77. TLC: Silica GF (90/10/1/1 of $CH_2Cl_2$/MeOH/$H_2O$/HoAc) Rf=0.54.

EXAMPLE 9

N-9H-Pyrido(3,4-b)indol-3-yl benzene Acetamide

3-Amino N-9H pyrido(3,4-b)indole was treated according to the procedure of Example 3 using phenylacetyl chloride in place of p-chlorobenzoylchloride. Flash chromatography of the crude product on silica gel ($CH_2Cl_2$/EtOAc 60/40) gave the title compound as tan crystals from ether. M.p. 182°–5° C. NMR: consistent with structural assignment. HPLC: 100% pure. M.S.: Molecular ion observed at 301 m/e.

Anal Calc'd for: $C_{19}H_{15}N_3O$: C, 75.73; H, 5.02; N, 13.95. Found: C, 76.05; H, 5.19; N, 13.94. TLC: Silica GF (90/10/1/1 of CH₂Cl₂/MeOH/H₂O/HoAc) Rf=0.50.

EXAMPLE 10

N-9H-Pyrido(3,4-b)indol-3-yl benzene Propanamide

3-Amino-N 9H pyrido(3,4-b)indole was treated according to the procedure of Example 3 using hydrocinnamoyl chloride in place of p-chlorobenzoylchloride. Flash chromatography of the crude product on silica gel (CH₂Cl₂/EtOAc 60/40) gave the title compound as a white fluffy solid from ether. M.p. 105°-10° C. NMR: consistent with structural assignment. HPLC: 100% pure. M.S.: Molecular ion observed at 315 m/e.

Anal Calc'd for: $C_{20}H_{17}N_3O$: C, 76.17; H, 5.43; N, 13.33. Found: C, 75.96; H, 5.55; N, 13.20. TLC: Silica GF (90/10/1/1 of CH₂Cl₂/MeOH/H₂O/HoAc) Rf=0.51.

What is claimed is:
1. Compound of formula I:

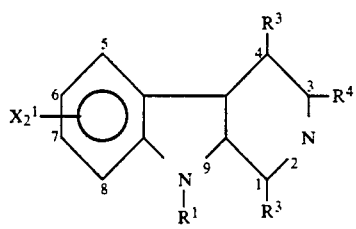

wherein:
each $X^1$ is independently selected from the group consisting of H, Cl, Br, F, I, NO₂, CF₃, NH₂, CH₃, C₁₋₄ straight or branched chain alkoxy, alkyl or alkylthio, and CN;
$R^1$ is H, C₁₋₄ straight or branched chain alkyl,

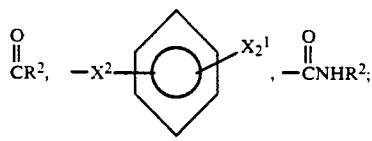

each $R^2$ is independently selected from the group consisting of C₁₋₄ linear or branched chain alkyl, phenyl,

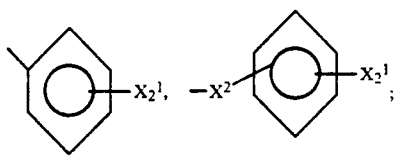

each $X^2$ is independently selected from the group consisting of C₁₋₄ linear or branched alkylidene;
each $R^3$ is independently selected from the group consisting of: H, C₁₋₄ linear or branched alkyl,

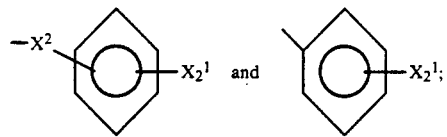

$R^4$ is selected from the group consisting of:

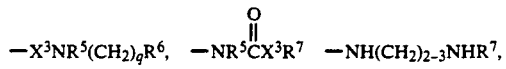
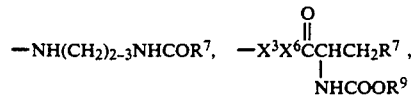
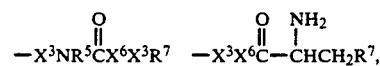
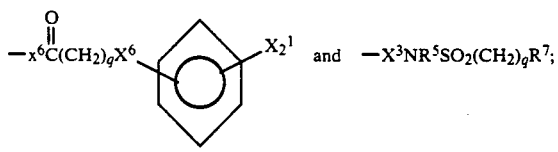

$R^5$ is H or C₁₋₄ linear or branched chain alkyl;
$R^6$ is alpha or beta naphthyl or 2-indolyl;
q is 0–4;
$R^7$ is α- or β-naphthyl, substituted or unsubstituted phenyl (wherein the substituents may be 1 to 2 of halo, —NO₂, —OH, —X³NR¹⁰R¹¹, C₁₋₄ linear or branched chain alkyl, CF₃, CN, SCF₃, C≡CH, CH₂SCF₃,

OCHF₂, SH, SPh, PO₃H, C₁₋₄ linear or branched chain alkoxy, C₁₋₄ linear or branched chain alkylthio or COOH), 2-, 3-, 4-pyridyl,

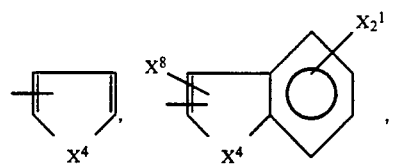
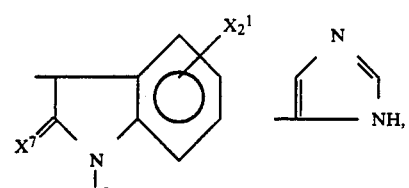
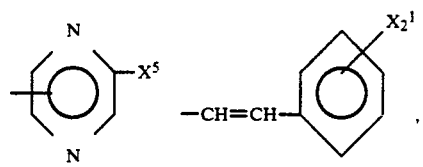

-continued

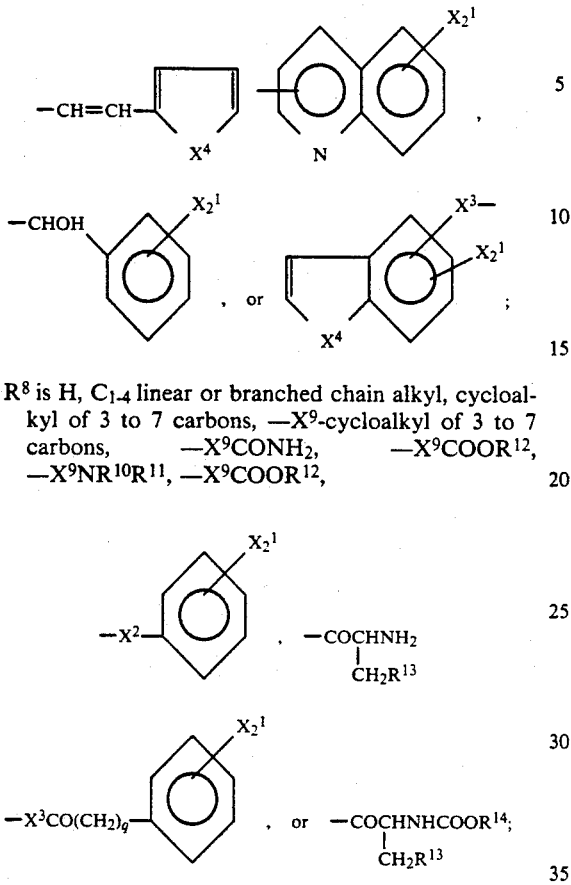

$R^8$ is H, $C_{1-4}$ linear or branched chain alkyl, cycloalkyl of 3 to 7 carbons, —$X^9$-cycloalkyl of 3 to 7 carbons, —$X^9CONH_2$, —$X^9COOR^{12}$, —$X^9NR^{10}R^{11}$, —$X^9COOR^{12}$, —$X^2$—⟨phenyl-$X_2^1$⟩, —COCHNH$_2$ | CH$_2$R$^{13}$ —$X^3CO(CH_2)_q$—⟨phenyl-$X_2^1$⟩, or —COCHNHCOOR$^{14}$ | CH$_2$R$^{13}$ $R^9$ is $C_{1-4}$ linear or branched chain alkyl or phenyl $C_{1-4}$ linear or branched chain alkyl;

$R^{10}$ and $R^{11}$ are independently $R^{12}$;

$R^{12}$ is H, $C_{1-4}$ linear or branched chain alkyl, cycloalkyl of 3 to 7 carbons, substituted or unsubstituted phenyl, or substituted or unsubstituted phenyl $C_{1-4}$ linear or branched chain alkyl wherein the phenyl or phenyl $C_{1-4}$ linear or branched chain alkyl substituents may be 1 to 2 of halo, $C_{1-4}$ linear or branched chain alkyl, $C_{1-4}$ linear or branched chain alkoxy, nitro, or $CF_3$;

$R^{13}$ and $R^{14}$ are independently $C_{1-4}$ linear or branched chain alkyl or cycloalkyl of 3 to 7 carbons;

$X^3$ is absent or $C_{1-4}$ linear or branched alkylidene;

$X^4$ is S, O, $CH_2$ or $NR^8$;

$X^5$ is H, $CF_3$, CN, —$COOR^{12}$, $NO_2$ or halo; each $X^6$ is independently $NR^5$ or O;

$X^7$ is O or HH;

$X^8$ is H or $C_{1-4}$ linear or branched chain alkyl;

$X^9$ is $C_{1-4}$ linear or branched chain alkylidene; with the proviso that when $X^1$ is H, $R^1$ is H, each $R^3$ is H, then $R^4$ is not

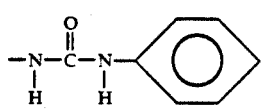

or the pharmaceutically acceptable salts thereof.

2. A compound of claim 1 wherein $X^1$ is H, $R^1$ is H, $R^3$ is H and $R^4$ is

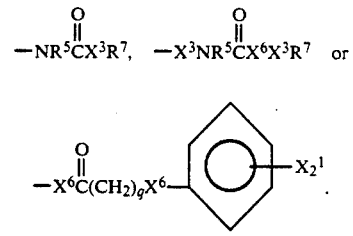

3. A method of antagonizing the binding of cholecystokinins to cholecystokinin receptors or antagonizing the binding of gastrin to gastrin receptors which comprises contacting said cholecystokinin receptors or said gastrin receptors, respectively, with a compound represented by formula I:

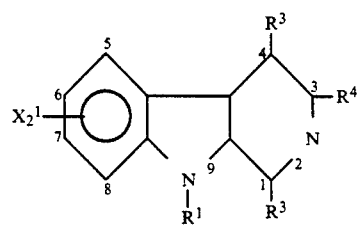

wherein:
each $X^1$ is independently selected from the group consisting of H, Cl, Br, F, I, $NO_2$, $CF_3$, $NH_2$, $CH_3$, $C_{1-4}$ straight or branched chain alkoxy, alkyl or alkylthio, and CN;

$R^1$ is H, $C_{1-4}$ straight or branched chain alkyl,

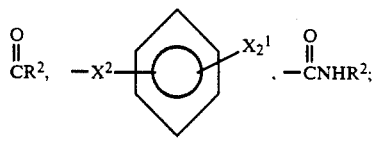

each $R^2$ is independently selected from the group consisting of $C_{1-4}$ linear or branched chain alkyl, phenyl,

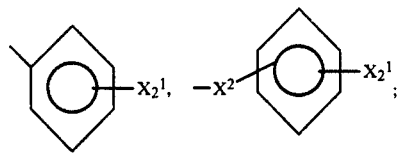

each $X^2$ is independently selected from the group consisting of $C_{1-4}$ linear or branched alkylidene;

each $R^3$ is independently selected from the group consisting of: H, $C_{1-4}$ linear or branched alkyl,

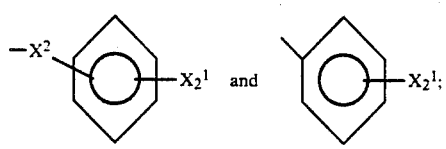

$R^4$ is selected from the group consisting of:

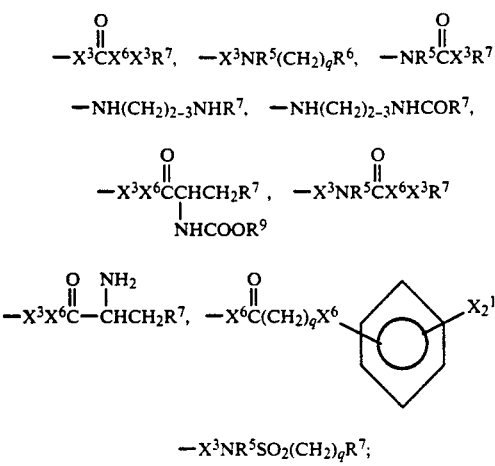

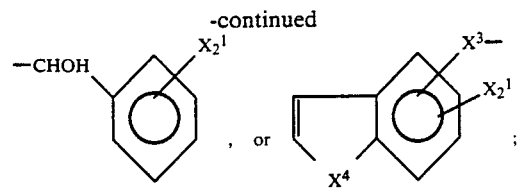

$R^5$ is H or $C_{1-4}$ linear or branched chain alkyl;
$R^6$ is alpha or beta naphthyl or 2-indolyl;
q is 0-4;
$R^7$ is α- or β-naphthyl, substituted or unsubstituted phenyl (wherein the substituent is 1 to 2 of halo, —$NO_2$, —OH, —$X^3NR^{10}R^{11}$, $C_{1-4}$ linear or branched chain alkyl, $CF_3$, CN, $SCF_3$, C≡CH, $CH_2SCF_3$,

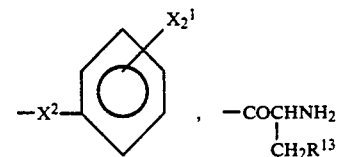

$OCHF_2$, SH, SPh, $PO_3H$, $C_{1-4}$ linear or branched chain alkoxy, $C_{1-4}$ linear or branched chain alkylthio or COOH), 2- 3-, 4-pyridyl,

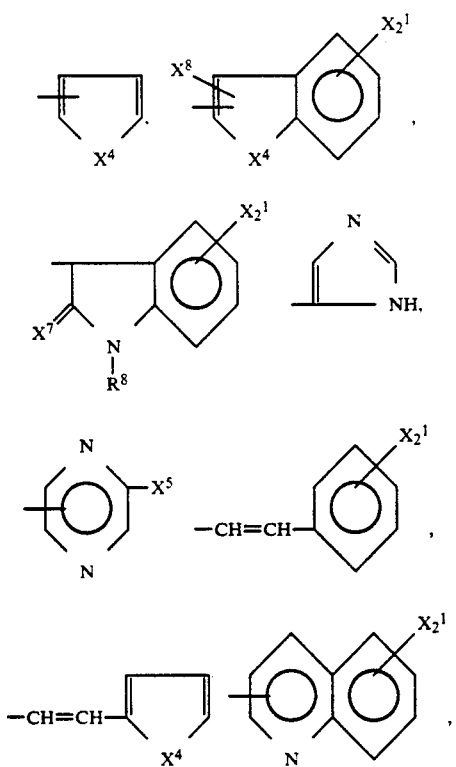

-continued

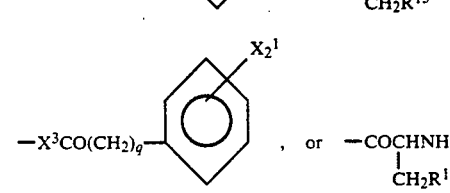

$R^8$ is H, $C_{1-4}$ linear or branched chain alkyl, cycloalkyl of 3 to 7 carbons, —$X^9$-cycloalkyl of 3 to 7 carbons, —$X^9CONH_2$, —$X^9COOR^{12}$, —$X^9NR^{10}R^{11}$, —$X^9COOR^{12}$,

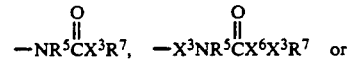

$R^9$ is $C_{1-4}$ linear or branched chain alkyl or phenyl $C_{1-4}$ linear or branched chain alkyl;
$R^{10}$ and $R^{11}$ are independently $R^{12}$;
$R^{12}$ is H, $C_{1-4}$ linear or branched chain alkyl, cycloalkyl of 3 to 7 carbons, substituted or unsubstituted phenyl, or substituted or unsubstituted phenyl $C_{1-4}$ linear or branched chain alkyl wherein the phenyl or phenyl $C_{1-4}$ linear or branched chain alkyl substituent may be 1 to 2 of halo, $C_{1-4}$ linear or branched chain alkyl, $C_{1-4}$ linear or branched chain alkoxy, nitro, or $CF_3$;
$R^{13}$ and $R^{14}$ are independently $C_{1-4}$ linear or branched chain alkyl or cycloalkyl of 3 to 7 carbons;
$X^3$ is absent or $C_{1-4}$ linear or branched alkylidene;
$X^4$ is S, O, $CH_2$ or $NR^8$;
$X^5$ is H, $CF_3$, CN, —$COOR^{12}$, $NO_2$ or halo; each $X^6$ is independently $NR^5$ or O;
$X^7$ is O or HH;
$X^8$ is H or $C_{1-4}$ linear or branched chain alkyl; and
$X^9$ is $C_{1-4}$ linear or branched chain alkylidene; or the pharmaceutically acceptable salts thereof.

4. The method of claim 3 wherein $X^1$ is H, $R^1$ is H, $R^3$ is H and $R^4$ is

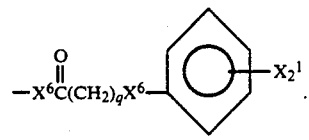

5. The method of claim 3 wherein a therapeutically effective amount of said compound is utilized for treating gastrointestinal disorders, central nervous system disorders or regulating appetite in animals.

6. A pharmaceutical composition useful for antagonizing the binding of cholecystokinins to cholecystokinin receptors or antagonizing the binding of gastrin to gastrin receptors which comprises a therapeutically effective amount of a compound of claim 1 and an acceptable pharmaceutical carrier.

* * * * *